United States Patent
Nakamura et al.

(10) Patent No.: US 7,161,021 B2
(45) Date of Patent: Jan. 9, 2007

(54) PROCESS FOR PRODUCING A POLYNITRILE COMPOUND

(75) Inventors: Kenichi Nakamura, Niigata (JP); Shuji Ebata, Niigata (JP); Fumio Tanaka, Niigata (JP); Takuji Shitara, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 58 days.

(21) Appl. No.: 10/313,022

(22) Filed: Dec. 6, 2002

(65) Prior Publication Data

US 2003/0114701 A1   Jun. 19, 2003

(30) Foreign Application Priority Data

Dec. 13, 2001 (JP) ............................. 2001-379793

(51) Int. Cl.
  *C07C 253/18* (2006.01)
  *C07C 255/04* (2006.01)
(52) U.S. Cl. ...................................... 558/327; 558/419
(58) Field of Classification Search ................ 558/327, 558/419
   See application file for complete search history.

(56) References Cited

U.S. PATENT DOCUMENTS 3,246,028 A * 4/1966 Tolanci et al. ............... 558/327
3,479,385 A   11/1969 Huibers
3,497,545 A   2/1970 Yoo et al.
3,732,280 A   5/1973 Norton
5,015,756 A * 5/1991 Ramachandran et al. ... 558/320

FOREIGN PATENT DOCUMENTS

EP   1113001 A2 *  7/2001

* cited by examiner

*Primary Examiner*—Golam M. M. Shameem
*Assistant Examiner*—Ebenezer Sackey
(74) *Attorney, Agent, or Firm*—Antonelli, Terry, Stout and Kraus, LLP.

(57) ABSTRACT

In a process for producing a polynitrile compound comprising introducing a polysubstituted organic compound (POC) which is a carbon ring or heterocyclic compounds having a plurality of organic substituents into a reactor with ammonia and a gas containing oxygen and ammoxidizing POC in the presence of a catalyst, at least a portion of the unreacted POC and a mononitrile compound of an intermediate product in the reaction gas discharged from the reactor is separated, recovered and recycled to the reactor so that the flow rate of the mononitrile compound at the outlet of the reactor is 2 to 16% by mole of the total flow rate of POC and the mononitrile compound supplied to the reactor.

Burning reaction of the side reaction is suppressed and the loss of POC can be decreased without adverse effects on productivity and the polynitrile compound can be obtained at a high yield.

13 Claims, 1 Drawing Sheet

PROCESS FOR PRODUCING A POLYNITRILE COMPOUND

BACKGROUND OF THE INVENTION

1. Field of the Invention

The present invention relates to a process for producing a polynitrile compound comprising reacting a carbon ring or heterocyclic compound having a plurality of organic substituents with ammonia and a gas containing oxygen. More particularly, the present invention relates to a process for producing a carbon ring or heterocyclic dinitrile compound from a carbon ring or heterocyclic compound having two organic substituents.

2. Description of the Related Arts

Polynitrile compounds and, in particular, carbon ring dinitrile compounds are useful as raw materials for synthetic resins and agricultural chemicals and as intermediate compounds for amines and isocyanates. Heterocyclic dinitrile compounds are useful as intermediate compounds for drugs and additives for feed and food.

The process of reacting an organic compound such as a carbon ring or heterocyclic compound having organic substituents with ammonia and a gas containing oxygen is called ammoxidation and, in general, nitrile compounds are produced in accordance with a gas phase catalytic reaction.

It is known that catalysts containing vanadium, molybdenum or iron are used for the ammoxidation. For example, in Japanese Patent Application Laid-Open No. Heisei 11(1999)-209332, a process for ammoxidizing carbon ring and heterocyclic compounds having alkyl groups as substituents in the presence of a catalyst containing oxides of V, Cr, B and Mo is described. In Japanese Patent Application Laid-Open No. Heisei 9(1997)-71561, a process for producing dicyanobenzene by the ammoxidation of xylene in the presence of a catalyst containing oxides of Fe, Sb and V is described.

When a nitrile compound is produced by the ammoxidation, in general, the temperature of the reaction, the amount of ammonia, the amount of oxygen and the time of contact are suitably selected so that the maximum yield of the nitrile compound is obtained. Actually, relatively severe conditions are selected so that the conversion of the carbon ring or heterocyclic compound of the raw material increases. However, the burning reaction takes place as the side reaction under such severe conditions and causes a loss of the raw material. Therefore, a process which can prevent the burning reaction and decrease the loss of the raw material has been desired.

It is possible that the conversion of the raw material is suppressed at a small value and the unreacted raw material is recycled to suppress the side reaction. However, this process has a drawback in that the one-pass yield of the nitrile compound decreases and productivity decreases.

SUMMARY OF THE INVENTION

The present invention has an object of providing a process which, in the process for producing a polynitrile compound by ammoxidation of a carbon ring or heterocyclic compound having a plurality of organic substituents (hereinafter, referred to as a polysubstituted organic compound) with ammonia and a gas containing oxygen in accordance with the gas phase catalytic reaction, suppresses the burning reaction of the side reaction without adverse effects on productivity, decreases the loss of the raw material and provides the polynitrile compound of the object compound at a high yield.

As the result of intensive studies by the present inventors to achieve the above object, it was found that, when at least a portion of the unreacted polysubstituted organic compound and a mononitrile compound of an intermediate product was separated from the reaction gas discharged from the reactor, recovered and recycled to the reactor and the reaction was controlled in a manner such that the flow rate of the mononitrile compound in the reaction gas discharged from the reactor was in a specific range, the loss of the raw material due to the burning reaction was suppressed without adverse effects on productivity and the polynitrile compound could be produced very efficiently at a high yield and excellent productivity. The present invention has been completed based on the above knowledge.

The present invention provides a process for producing a polynitrile compound which comprises introducing a polysubstituted organic compound selected from carbon ring compounds having a plurality of organic substituents and heterocyclic compounds having a plurality of organic substituents into a reactor in combination with ammonia and a gas containing oxygen and ammoxidizing the polysubstituted organic compound in a presence of a catalyst, wherein at least a portion of the unreacted polysubstituted organic compound and a mononitrile compound of an intermediate product which are contained in a reaction gas discharged from the reactor is separated, recovered and recycled to the reactor in a manner such that a flow rate by mole of the mononitrile compound at an outlet of the reactor is adjusted in a range of 2 to 16% based on a total of flow rates by mole of the polysubstituted organic compound and the mononitrile compound supplied to the reactor.

BRIEF DESCRIPTION OF THE DRAWINGS

In FIG. 1, 1 means a reactor of ammoxidation, 2 means a part for collecting reaction products and 3 means a distillation column.

DESCRIPTION OF THE PREFERRED EMBODIMENTS

Figure 1:
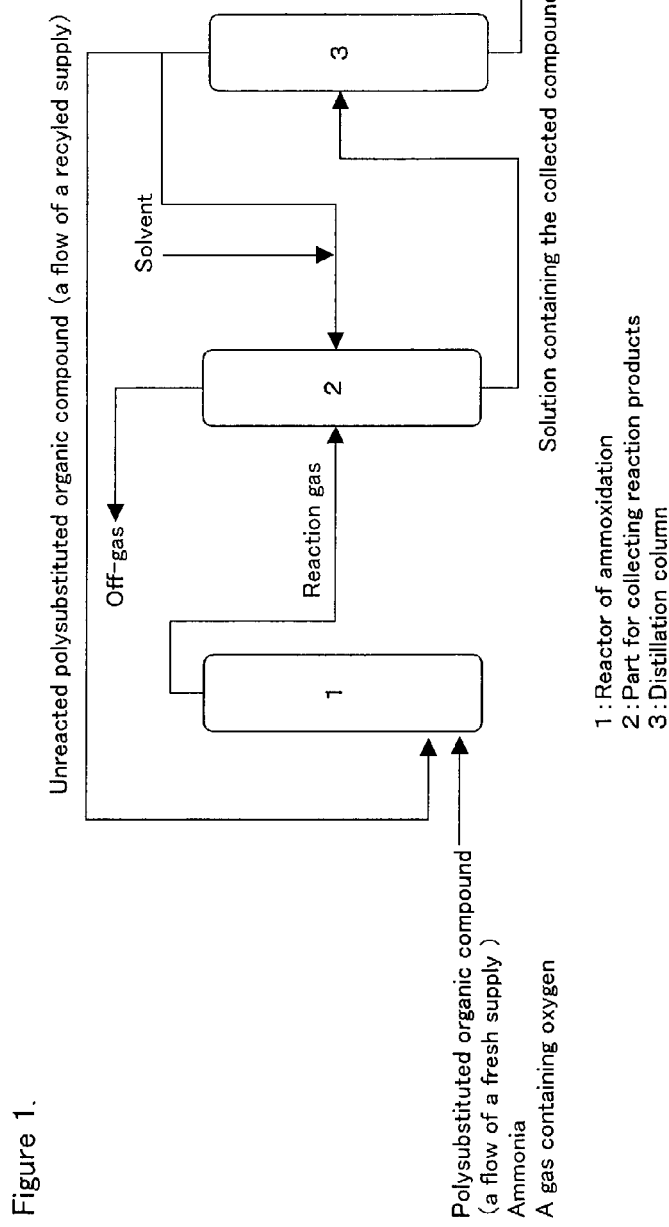
FIG. 1 shows a flow diagram exhibiting an embodiment of the process for producing a polynitrile compound of the present invention. In this embodiment, the ammoxidation is conducted in accordance with the reaction using a fluidized bed. The reaction gas discharged from the reactor is brought into contact with a mononitrile compound used as the solvent and the reaction products are collected. The unreacted polysubstituted organic compound and the mononitrile compound are recovered by distillation from the solution containing the collected products.

The carbon ring compound having a plurality of organic substituents which is used as the raw material in the present invention is a carbon ring compound having a carbon ring such as benzene ring, naphthalene ring, anthracene ring, cyclohexene ring, cyclohexane ring, dihydronaphthalene ring, tetraline ring and decaline ring and organic substituents such as methyl group, ethyl group, propyl group, formyl group, acetyl group, hydroxymethyl group and methoxycarbonyl group as the side chains on the carbon ring. The plurality of organic substituents may be the same with or different from each other. The carbon ring compound may further have atoms and groups which do not take part in the ammoxidation such as a halogen atom, hydroxyl group, amino group, nitro group, alkoxyl group and phenyl group.

Examples of the carbon ring compound having organic substituents include xylene, dimethyl-naphthalene, dimethyltetraline, chloroxylene, dimethylanisole, pseudocumene and mesitylene. Polynitrile compounds are obtained by the ammoxidation of these compounds.

The heterocyclic compound having a plurality of organic substituents which is used as the raw material is a heterocyclic compound having a heterocyclic ring such as furan ring, pyrrol ring, indole ring, thiophene ring, pyrazole ring, imidazole ring, oxazole ring, pyran ring, pyridine ring, quinoline ring, isoquinoline ring, pyrroline ring, pyrrolidine ring, imidazoline ring, imidazolidine ring, piperidine ring and piperadine ring and a plurality of organic substituents such as those described above as the side chains on the heterocyclic ring. The heterocyclic compound may further comprise as the side chains thereof atoms and groups which do not take part in the ammoxidation such as those described above for the carbon ring compound. Examples of the heterocyclic compound include dimethylpyridine and dimethylpyrazine.

The polysubstituted organic compounds may be used singly or as a mixture of two or more. The present invention is advantageously applied to producing isophthalonitrile from meta-xylene having two methyl groups on the benzene ring among the above compounds.

In the present invention, the polynitrile compound is produced by the ammoxidation of the above polysubstituted organic compound with ammonia and a gas containing oxygen in accordance with the gas phase catalytic reaction. For the ammoxidation, for example, a fixed bed reactor, a moving bed reactor or a fluidized bed reactor may be used. The fluidized bed catalyst is preferable from the standpoint of controlling the temperature of the reaction and cost of the apparatus. The catalyst used in the present invention is not particularly limited as long as the catalyst is suitable for the ammoxidation in accordance with the gas phase catalytic reaction. As the catalyst, for example, catalysts comprising an oxide of at least one element selected from vanadium, molybdenum and iron are preferable.

When the fluidized bed catalyst is used, the particle diameter of the catalyst is in the range of 10 to 300 μm. The average particle diameter is in the range of 30 to 200 μm and preferably in the range of 40 to 100 μm. The bulk density of the catalyst is in the range of 0.5 to 2 $g/cm^3$ and preferably in the range of 0.7 to 1.5 $g/cm^3$.

As the gas containing oxygen used for the ammoxidation, in general, the air is preferable. The air may be used after the content of oxygen is increased or may be used in combination with a diluent such as nitrogen gas and carbon dioxide gas. The amount of oxygen expressed as the ratio of the amount by mole of oxygen to the amount by mole of the organic substituent in the polysubstituted organic compound ($O_2$/organic substituent) is 0.75 or more, preferably in the range of 1 to 25 and most preferably in the range of 1.5 to 5. When the amount of the air is less than the above range, the yield of the nitrile compound decreases. When the amount of the air exceeds the above range, the space-time yield decreases.

In the present invention, ammonia of the industrial grade can be used as ammonia. The amount of ammonia expressed as the ratio of the amount by mole of ammonia to the amount by mole of the organic substituent in the polysubstituted organic compound ($NH_3$/organic substituent) is in the range of 1 to 10 and preferably in the range of 3 to 7. When the amount of ammonia is less than the above range, the yield of the nitrile compound decreases. When the amount of ammonia exceeds the above range, industrial disadvantages arise since the loss or the cost of recovery of unreacted ammonia increases.

The pressure of the ammoxidation may be any of the atmospheric pressure, an added pressure and a reduced pressure. It is preferable that the pressure is in the range of around the atmospheric pressure to 0.2 MPa. The time of contact between the reaction gas and the catalyst is varied depending on the conditions such as the type of the polysubstituted organic compound of the raw material, amounts by mole of ammonia and the gas containing oxygen supplied for the reaction relative to the amount by mole of the polysubstituted organic compound and the temperature of the reaction. The time of contact is, in general, in the range of 0.5 to 30 seconds.

The temperature of the reaction is in the range of 300 to 500° C. and preferably in the range of 330 to 470° C. When the temperature is lower than the above range, a sufficient reaction rate is not obtained. When the temperature exceeds the above range, the amount of byproducts such as carbon dioxide and hydrogen cyanide increases and the yield of the polynitrile compound decreases.

In the present invention, at least a portion of and, preferably, the entire amount of the unreacted polysubstituted organic compound and the mononitrile compound of the intermediate product which are contained in the reaction gas discharged from the reactor is separated, recovered and recycled to the reactor in a manner such that the flow rate by mole of the mononitrile compound at the outlet of the reactor is adjusted in the range of 2 to 16% and preferably in the range of 3 to 14% based on the total of the flow rates by mole of the polysubstituted organic compound and the mononitrile compound supplied to the reactor.

When the flow rate by mole of the mononitrile compound at the outlet of the reactor is smaller than 2% based on the total of the flow rates by mole of the polysubstituted organic compound and the mononitrile compound supplied to the reactor, the yield decreases due to the increase in the burning reaction and a sufficient effect of recovering the unreacted polysubstituted organic compound and the mononitrile compound and recycling these compounds to the reactor to increase the yield is not obtained. When the above flow rate exceeds 16% by mole, the flow rate of the substances supplied by the recycling extremely increases due to the decrease in the space-time yield and productivity is adversely affected.

The temperature of the reaction, the amount of ammonia, the amount of oxygen and the time of contact are suitably adjusted so that the flow rate by mole of the mononitrile compound at the outlet of the reactor is adjusted in the range of 2 to 16% based on the total of the flow rates by mole of the polysubstituted organic compound and the mononitrile compound supplied to the reactor.

In the present invention, the polynitrile compound of the object compound, the unreacted polysubstituted organic compound and the mononitrile compound of the intermediate compound are separated from the reaction gas discharged at the outlet of the reactor and the unreacted polysubstituted organic compound and the mononitrile compound are recycled to the reactor of ammoxidation. Examples of the process for separating and recovering the unreacted raw material and the mononitrile compound from the reaction gas include the following three processes (1) to (3). (1) A process in which the reaction gas is brought into contact with an organic solvent and cooled so that the polynitrile compound, the unreacted polysubstituted organic compound and the mononitrile compound are collected with the solvent and the unreacted polysubstituted organic compound and the mononitrile compound are separated from the liquid containing the collected compounds in accordance with distillation or the like. (2) A process in which the reaction gas is brought into contact with water and cooled so that a slurry of the polynitrile compound in water and a liquid phase of an organic solvent containing the unreacted polysubstituted organic compound and the mononitrile compound are formed and the liquid phase of the organic solvent and the aqueous phase of the slurry are separated from each other by a method of liquid-liquid separation so that the unreacted polysubstituted organic compound and the mononitrile compound are separated. (3) A process in which, after the reaction gas is cooled so that solid precipitates of the polynitrile compound are obtained and the obtained solid precipitates are separated, the residual reaction gas is cooled to a very low temperature so that the unreacted polysubstituted organic compound and the mononitrile compound are condensed into liquids and separated.

In process (1), an organic solvent such as an alkylbenzene, a heterocyclic compound, a carbon ring nitrile and a heterocyclic nitrile is used as the above solvent. It is preferable that an intermediate product of the ammoxidation such as a mononitrile compound is used since the number of the substances in the process does not increase. For example, it is preferable that meta-tolunitrile is used when isophthalonitrile is obtained from meta-xylene. Examples of the process for bringing the reaction gas into contact with the organic solvent include direct addition of the organic solvent into a flow of the reaction gas by spraying the organic solvent or the like method and direct contact of the organic solvent with the reaction gas by introducing the reaction gas into a vessel containing the organic solvent. The polynitrile compound, the unreacted polysubstituted organic compound and the mononitrile compound contained in the reaction gas are collected with the solvent and recovered as a solution.

Using the recovered solution containing the collected compounds, the unreacted polysubstituted organic compound and the mononitrile compound are separated from the polynitrile compound, the organic solvent and other components in accordance with a conventional method of separation such as distillation and crystallization. At least a portion of the unreacted polysubstituted organic compound and the mononitrile compound which are separated is recycled to the reactor and used for the ammoxidation. After the unreacted polysubstituted organic compound and the mononitrile compound are separated from the solution containing the collected compounds, the residual solution contains the polynitrile compound, the organic solvent and components having higher boiling points. These compounds are suitably separated and recovered in accordance with a conventional method of separation such as distillation and crystallization, where necessary.

On the other hand, after the reaction gas has been brought into contact with the organic solvent, the resultant residual gas is discharged as an off-gas, which contains gas components insoluble in the organic solvent and the vapor of the organic solvent. It is possible that the organic solvent contained in the off-gas is further separated and recovered in accordance with a conventional method such as cooling at a very low temperature so that the loss of the organic solvent contained in the off-gas is prevented.

When the mononitrile compound is used as the solvent, the residual solution which is obtained after separation of the polynitrile compound from the solution containing the collected compounds and contains the unreacted polysubstituted organic compound and the mononitrile compounds as the main components can be used directly for the ammoxidation. The residual solution may be used also as the solvent for the collection which is brought into contact with the reaction gas.

FIG. 1 shows a flow diagram exhibiting an embodiment of the process of the present invention. In this embodiment, the ammoxidation is conducted in accordance with the reaction using the fluidized bed. The reaction gas discharged from the reactor is brought into contact with a mononitrile compound used as the solvent and the reaction products are collected. The unreacted polysubstituted organic compound and the mononitrile compound are recovered by distillation from the solution containing the collected products. In FIG. 1, 1 means a reactor of ammoxidation, 2 means a part for collecting reaction products, 3 means a distillation column.

In FIG. 1, a reactor of ammoxidation 1 is packed with a layer of the fluidized catalyst. To the reactor, the gas containing oxygen, ammonia, the polysubstituted organic compound (a flow of a fresh supply) and the unreacted polysubstituted organic compound and the mononitrile compound which are recycled (a flow of a recycled supply) are supplied and the ammoxidation is conducted. A cooling tube is disposed at the inside of the reactor and the surface of the fluidized catalyst bed is placed at a lower portion of the upper end portion of the cooling tube. After particles of the catalyst in the reaction gas are separated by a catalyst cyclone and returned to the fluidized catalyst bed via a tube for returning the catalyst, the reaction gas is discharged via a tube for discharge. The reaction gas discharged from the reactor contains the unreacted polysubstituted organic compound, the polynitrile compound, the mononitrile compound, ammonia, hydrogen cyanide, carbon dioxide, water, carbon monoxide, nitrogen and oxygen. The reaction gas is transferred to a part for collecting reaction products 2 of the next step. In the part for collecting reaction products 2, the reaction gas and the mononitrile compound used as the solvent for collecting the reaction products are brought into contact with each other and the polynitrile compound, the unreacted polysubstituted organic compound and the mononitrile compound contained in the reaction gas are collected. The solution containing these compounds is recovered as the solution containing collected compounds. Portions of the mononitrile compound and the unreacted polysubstituted organic compound which are vaporized are cooled and separated from hydrogen cyanide, ammonia, carbon dioxide and water and recovered so as to be used as a portion of the solution for collecting reaction products. An off-gas from which the unreacted polysubstituted organic compound and the mononitrile compound are sufficiently separated and which comprises nitrogen, oxygen and carbon monoxide is discharged at an outlet for a gas of the part for collecting reaction products. The solution containing the collected compounds is introduced into a distillation column 3. In accordance with distillation, the unreacted polysubstituted organic compound and the mononitrile compound are recovered at the top of the column and a flow containing the polynitrile compound is recovered at the bottom of the column. The unreacted polysubstituted organic compound and the mononitrile compound obtained at the top of the column are supplied to the part for collecting reaction products 2 so that these compounds are used as the solvent for collecting reaction products and also supplied to the reactor of ammoxidation 1 as a flow of recycling so that these compounds are used for the reaction.

As shown clearly in the following examples, in accordance with the process of the present invention, burning reaction of the side reaction is suppressed and the loss of the polysubstituted organic compound of the raw material can be decreased without adverse effects on productivity. Thus, the nitrile compound of the object compound can be obtained at a high yield.

EXAMPLES

The present invention will be described more specifically with reference to Example and Comparative Example in the following. However, the present invention is not limited to Example and Comparative Example.

<Preparation of a Catalyst>

To 229 g of vanadium pentoxide $V_2O_5$, 500 ml of water was added. The resultant mixture was heated at 80 to 90° C. and 477 g of oxalic acid was added under sufficient stirring and dissolved. Separately, 400 ml of water was added to 963 g of oxalic acid and the resultant mixture was heated at 50 to 60° C. To the obtained solution, a solution obtained by adding 252 g of chromic acid anhydride $CrO_3$ into 200 ml of water was added under sufficient stirring and dissolved. To the solution of vanadium oxalate obtained above, the solution of chromium oxalate obtained above was mixed at 50 to 60° C. and a vanadium-chromium solution was obtained. To the obtained solution, a solution obtained by dissolving 41.1 g of phosphomolybdic acid $H_3(PMo_{12}O_{40}) \cdot 20H_2O$ into 100 ml of water was added. To the resultant solution, a solution obtained by dissolving 4.0 g of potassium acetate $CH_3COOK$ into 100 ml of water was added and, then, 2,500 g of a 20% by weight aqueous silica sol (containing 0.02% by weight of $Na_2O$) was added. To the obtained slurry, 78 g of boric acid $H_3BO_3$ was added and sufficiently mixed. The resultant fluid was concentrated by heating until the amount of the fluid became about 3,800 g. The obtained catalyst solution was dried by spraying while the temperature at the inlet was kept at 250° C. and the temperature at the outlet was kept at 130° C. The catalyst obtained after the drying by spraying was dried in a drier at 130° C. for 12 hours and calcined at 400° C. for 0.5 hours and, then, at 550° C. for 8 hours under a stream of the air and a fluidized catalyst was prepared. The catalyst contained the components in amounts such that the ratio by atom of the components V:Cr:B:Mo:P:Na:K was 1:1:0.5:0.086:0.007:0.009:0.020 and the concentration of the catalyst components in the fluidized catalyst was 50% by weight.

Comparative Example

The ammoxidation of meta-xylene was conducted using the reactor of ammoxidation shown in FIG. 1. The reactor of ammoxidation was packed with 2.3 tons of the fluidized catalyst prepared above. The air, meta-xylene (MX) and ammonia gas were preheated at 180° C. and supplied to the reactor. The amount of supply of MX was 242 kg/hr, the amount of supply of ammonia was 333 kg/hr and the amount of supply of the air was 1,280 Nm³/hr. The reaction was conducted under a pressure of the reaction of 0.08 MPa and isophthalonitrile (IPN) was obtained. When the temperature of the reaction was adjusted, the yield of IPN showed the maximum value of 82.0% by mole at the temperature of the reaction of 432° C. The yield of the mononitrile compound (MTN) was 0.9% under this condition.

Under the above condition, the entire amounts of the unreacted MX and MTN contained in the reaction gas were separated, recovered and recycled to the reactor of ammoxidation. The amount of supply of MX was 242.3 kg/hr, the amount of supply of MTN was 2.4 kg/hr, the amount of supply of ammonia was 333 kg/hr and the amount of supply of the air was 1,280 Nm³/hr. The amount of the fresh supply of MX (the flow rate of the fresh supply) was 242 kg/hr, the flow rate of recycled MX was 0.3 kg/hr and the flow rate of recycled MTN was 2.4 kg/hr. The flow rate of the mononitrile compound at the outlet of the reactor was 0.9% by mole based on the total of the flow rates of the polysubstituted organic compound and the mononitril compound supplied to the reactor.

As the result of the analysis of the reaction gas discharged from the reactor, it was found that the reaction gas contained 0.3 kg/hr of MX, 242 kg/hr of IPN and 2.4 kg/hr of MTN.

The above results show that the balance between the amounts of the components was achieved when the amount of the recycled MX was 0.3 parts by mole, the amount of the fresh supply of MX was 100 parts by mole and the amount of the recycled MTN was 2.4 parts by mole. The yield of IPN was 82.8% by mole based on the amount of the fresh supply of MX. The space-time yield of IPN was 242 kg/hr.

Example 1

The ammoxidation of meta-xylene was conducted using the reactor of ammoxidation shown in FIG. 1. The reactor of ammoxidation was packed with 2.3 tons of the fluidized catalyst prepared above. The air, meta-xylene (MX) and ammonia gas were preheated at 180° C. and supplied to the reactor. The amount of supply of MX was 266 kg/hr, the amount of supply of MTN was 40.0 kg/hr, the amount of supply of ammonia was 412 kg/hr and the amount of supply of the air was 1,570 Nm³/hr. The reaction was conducted under a pressure of the reaction of 0.08 MPa and isophthalonitrile (IPN) was obtained. The temperature of the reaction was adjusted at 427° C. The amount of the fresh supply (the flow rate of the fresh supply) of MX was 241.8 kg/hr which was about the same as that in Comparative Example, the flow rate of recycled MX was 24.2 kg/hr and the flow rate of recycled MTN was 40.0 kg/hr. The flow rate of the mononitrile compound at the outlet of the reactor was 12.0% by mole based on the total of the flow rates of the polysubstituted organic compound and mononitrile compound supplied to the reactor.

As the result of the analysis of the reaction gas, it was found that the amount of MX was 24.2 kg/hr, the amount of IPN was 257.2 kg/hr and the amount of MTN was 40.0 kg/hr.

The above results show that the balance between the amounts of the components was achieved when the amount of the recycled MX was 10 parts by mole, the amount of the fresh supply of MX was 100 parts by mole and the amount of the recycled MTN was 15 parts by mole. The yield of IPN was 88.1% by mole based on the amount of the fresh supply of MX. The space-time yield of IPN was 257.2 kg/hr. The yield increased remarkably from that in Comparative Example without adverse effects on the space-time yield.

Example 2

The ammoxidation of meta-xylene was conducted using the reactor of ammoxidation shown in FIG. 1. The reactor of ammoxidation was packed with 2.3 tons of the fluidized catalyst prepared above. The air, meta-xylene (MX) and ammonia were preheated at 180° C. and supplied to the reactor. The amount of supply of MX was 245.6 kg/hr, the amount of supply of MTN was 10.7 kg/hr, the amount of supply of ammonia was 350 kg/hr and the amount of supply of the air was 1,320 Nm³/hr. The reaction was conducted under a pressure of the reaction of 0.08 MPa and isophthalonitrile (IPN) was obtained. The temperature of the reaction was adjusted at 427° C. The amount of the fresh supply (the flow rate of the fresh supply) of MX was 242 kg/hr which was the same as that in Comparative Example, the flow rate of recycled MX was 3.6 kg/hr and the flow rate of recycled MTN was 10.7 kg/hr. The flow rate of the mononitrile compound at the outlet of the reactor was 3.8% by mole based on the total of the flow rates of the polysubstituted organic compound and mononitrile compound supplied to the reactor.

As the result of the analysis of the reaction gas, it was found that the amount of MX was 3.6 kg/hr, the amount of IPN was 247 kg/hr and the amount of MTN was 10.7 kg/hr.

The above results show that the balance between the amounts of the components was achieved when the amount of the recycled MX was 1.5 parts by mole, the amount of the freshly supplied MX was 100 parts by mole and the amount of the recycled MTN was 4 parts by mole. The yield of IPN was 84.5% by mole based on the amount of the fresh supply of MX. The space-time yield of IPN was 247 kg/hr. The yield increased remarkably from that in Comparative Example without adverse effects on the space-time yield.

What is claimed is:

1. A process for producing a polynitrile compound which comprises introducing a polysubstituted organic compound selected from carbon ring compounds having a plurality of organic substituents and heterocyclic compounds having a plurality of organic substituents into a reactor in combination with ammonia and a gas containing oxygen and ammoxidizing the polysubstituted organic compound by gas phase reaction at 300° to 500° C. in a presence of a catalyst, wherein said carbon ring compounds have a carbon ring selected from the group consisting of benzene ring, naphthalene ring, anthracene ring, cyclohexene ring, cyclohexane ring, dihydronaphthalene ring, tetraline ring and decaline ring, wherein said heterocyclic compounds have a heterocyclic ring selected from the group consisting of furan ring, pyrrol ring, indole ring, thiophene ring, pyrazole ring, imidazole ring, oxazole ring, pyran ring, pyridine ring, quinoline ring, isoquinoline ring, pyrroline ring, pyrrolidine ring, imidazoline ring, piperidine ring and piperadine ring, wherein the organic substituents are selected from the group consisting of methyl, ethyl, propyl, formyl, acetyl, hydroxymethyl and methoxycarbonyl, and wherein a reaction gas discharged from the reactor contacts with an organic solvent, to provide a resultant liquid, and the resultant liquid is separated into the polynitrile compound and a mixture of unreacted polysubstituted organic compound and an intermediate mononitrile compound, and at least a portion of the unreacted polysubstituted organic compound and the intermediate mononitrile compound is recycled to the reactor in a manner such that a flow rate by mole of the mononitrile compound at an outlet of the reactor is adjusted in a range of 2 to 16% based on a total of flow rates by mole of the polysubstituted organic compound and the mononitrile compound supplied to the reactor.

2. A process according to claim 1, wherein the organic solvent with which the reaction gas is brought into contact is the mononitrile compound.

3. A process according to claim 1, wherein said polysubstituted organic compound is selected from the group consisting of xylene, dimethylnaphthalene, dimethyltetraline, chloroxylene, dimethylanisole, pseudocumene, mesitylene, dimethylpyridine and dimethylpyrazine.

4. A process according to claim 3, wherein the polysubstituted organic compound is a carbon ring compound having two organic substituents or a heterocyclic compound having two organic substituents and the polynitrile compound is a dinitrile compound.

5. A process according to claim 4, wherein the polysubstituted organic compound is meta-xylene, the mononitrile compound is meta-tolunitrile and the polynitrile compound is isophthalonitrile.

6. A process according to claim 3, wherein the gas phase reaction is performed in a range of 330° to 470° C.

7. A process according to claim 3, wherein said flow rate by mole of the mononitrile compound at the outlet of the reactor is adjusted in a range of 3 to 14% based on the total of flow rates by mole of the polysubstituted organic compound and the mononitrile compound supplied to the reactor.

8. A process according to claim 2, wherein said at least a portion of the unreacted polysubstituted organic compound and the intermediate mononitrile compound is directly recycled to the reactor after separation from the polynitrile compound.

9. A process according to claim 1, wherein said at least a portion of the unreacted polysubstituted organic compound and the intermediate mononitrile compound is directly recycled to the reactor after separation from the polynitrile compound.

10. A process according to claim 1, wherein the unreacted polysubstituted organic compound and the intermediate mononitrile compound are separated from ammonia in the reaction gas.

11. A process according to claim 3, wherein a substantially entire amount of the unreacted polysubstituted organic compound and the intermediate mononitrile compound which are contained in the reaction gas discharged from the reactor is separated, recovered and recycled to the reactor.

12. A process according to claim 3, wherein a catalyst comprising an oxide of at least one element selected from vanadium, molybdenum, and iron is used as the catalyst.

13. A process according to claim 3, wherein the ammoxidation is conducted using a fluidized bed.

* * * * *